United States Patent [19]

Okamoto et al.

[11] Patent Number: 4,979,900
[45] Date of Patent: Dec. 25, 1990

[54] ROOT CANAL STERILIZATION METHOD

[75] Inventors: Kazuhiro Okamoto; Masaharu Mogi, both of Kanagawa; Naotaka Kagawa; Yasuo Hino, both of Osaka, all of Japan

[73] Assignees: Sumitomo Electric Industries, Ltd., Osaka; Matsushita Electric Industrial Co., Ltd., Kadoma, both of Japan

[21] Appl. No.: 272,276

[22] Filed: Nov. 17, 1988

[30] Foreign Application Priority Data

Nov. 17, 1987 [JP] Japan ................. 62-290126

[51] Int. Cl.5 .............................. A61C 5/02
[52] U.S. Cl. ...................... 433/224; 433/81
[58] Field of Search ............... 433/32, 81, 215, 224, 433/229; 350/96.10, 96.26; 128/397, 398; 606/14, 15

[56] References Cited

U.S. PATENT DOCUMENTS

| 1,312,270 | 8/1919 | Russell | 606/28 |
| 1,550,197 | 8/1925 | Berry | 128/398 |
| 1,791,794 | 2/1931 | Chesney | 128/398 |
| 2,056,990 | 10/1936 | Symonds | 128/398 |
| 2,121,875 | 6/1938 | Kruse et al. | 433/224 |
| 3,712,984 | 1/1973 | Lienhard | 128/397 |
| 3,834,391 | 9/1974 | Block | 128/398 |
| 4,247,288 | 1/1981 | Yoshii et al. | 433/224 |
| 4,503,853 | 3/1985 | Ota et al. | 433/215 |
| 4,818,230 | 4/1989 | Myers et al. | 433/215 |
| 4,830,460 | 5/1989 | Goldenberg | 350/96.26 |

FOREIGN PATENT DOCUMENTS 3411366 10/1985 Fed. Rep. of Germany ...... 433/215

Primary Examiner—Gene Mancene
Assistant Examiner—Michael Lynch
Attorney, Agent, or Firm—Cushman, Darby & Cushman

[57] ABSTRACT

An apparatus and method for sterilizing a root canal in which the apparatus contains an light source for generating bactericidal ultraviolet rays and an optical fiber coupled to the light source for transmitting the ultraviolet rays to and emitting the rays from an emitting end of the optical fiber placed in the root canal. Also included in a fiber protecting pipe that both protects the fiber and allows the fiber to be easily guided into the root canal. A flexible tube disposed over the emitting end of the root canal protects the exposed end of the optical fiber. Also, an arrangement of two optical fibers allows various shaped fiber protecting pipes to be used and a hand held coupling device couples two optical fibers.

1 Claim, 2 Drawing Sheets

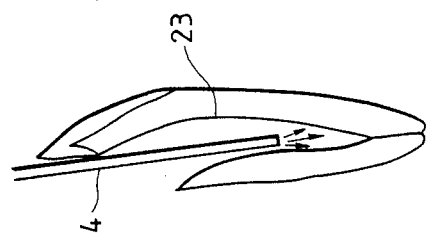
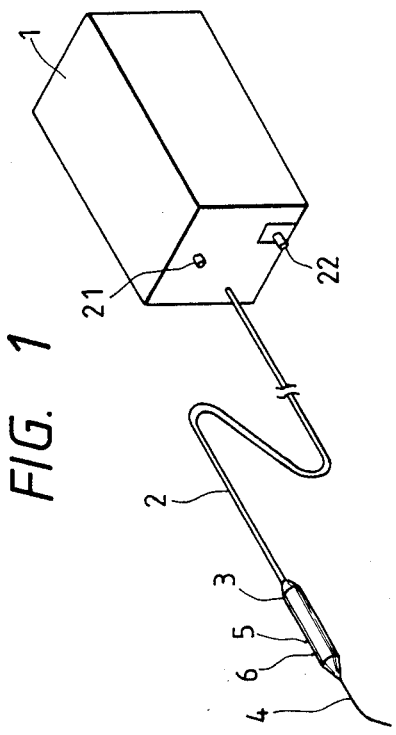
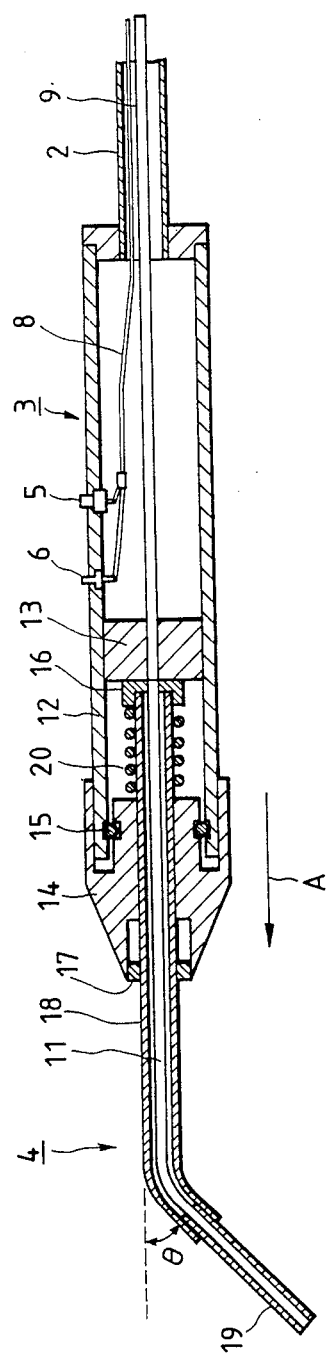

ROOT CANAL STERILIZATION METHOD

BACKGROUND OF THE INVENTION

1. The Field of the Art.

This invention relates to an apparatus for sterilizing a root canal and more specifically to a root canal sterilization apparatus that uses bactericidal ultra-violet rays to sterilize bacteria in the root canal.

2. Description of the Prior Art.

Bacteria in the root canal are important causal agents for apical periodontal inflammation. Therefore, for indodontal treatment, it is essential to remove bacteria from the root canal.

Previously, for removal of bacteria from the root canal, the following method has been used. Initially, the root canal is spread with a reamer or the like while being washed. Then, for the purpose of sterilizing the bacteria remaining in the root canal, a cotton plug impregnated with a sterilizing disinfectant, such as form cresol, is inserted into the root canal. Thereafter, washing of the root canal, and replacement of the cotton plug are carried out one or two more times. After this treatment, if no clinical symptom is detected and no abnormal clinical condition is observed inside the root canal, the final treatment of root canal filling is carried out.

However, the above-described method takes a relatively long time, one or two weeks, for sterilization, thus making the patient uncomfortable.

Furthermore, using this sterilization method, a high probability exists that after the root canal is filled, the inflammation will reoccur. This is because conventional chemical sterilization cannot completely sterilize the bacteria in the root canal and some bacteria still remain.

This difficulty may be eliminated by using a more effective germicide or by employing a method in which the root canal filling is carried out with a sterilizing disinfectant. However, these methods are undesirable because of the adverse effect of those chemicals when administered directly on the cells.

It is also well known that bactericidal ultraviolet rays (light 200 to 300 nm in wavelength) can sterilize bacteria. Use of the bacteriocidal ultraviolet rays is advantageous in that it will cause no danger of residual medicines.

However, the light source for generating such bacteriocidal ultraviolet rays is a bar-shaped lamp with an outside diameter of at least 10 mm and a length of 50 mm. With this size, it is impossible to insert it into the root canal spread (which has an inside diameter of about 1 to 1.5 mm). Also, a light source of this type usually incorporates mercury. Because of the toxicity of mercury, it is undesirable to insert it into the buccal cavity.

Therefore, bacteriocidal ultraviolet rays have not been used to sterilize bacteria in the root canal.

SUMMARY OF THE INVENTION

It is an object of the present invention to provide an apparatus that uses bactericidal ultraviolet rays to sterilize bacteria in the root canal.

It is another object of the present invention to provide an apparatus having that can be used for root canals that are located in various positions.

It is a further object of the present invention to provide an apparatus that can sterilize root canals and not damage easily.

In order to attain the above recited objects of the invention, among others, one embodiment of the present invention contains a light generating means that generates bactericidal ultraviolet rays that is connected to a light guide at one end. The other end of the light guide is coupled to a light emitting means with a hand piece that also allows easily handling of the light emitting means.

The emitting means contains an optical fiber over which is disposed a fiber protecting pipe. The fiber protecting pipe can be bent at different angles and functions as a guiding means. At the end perimeter of the emitting means, the optical fiber is connected to a flexible tube that serves as a covering means to protect the optical fiber from being damaged.

In another embodiment, the light guide and the emitting means use the same optical fiber and the hand piece then does not serve the coupling function.

BRIEF DESCRIPTION OF THE DRAWINGS

These and other advantages of the present invention may be appreciated from studying the following detailed description of the preferred embodiment together with the drawings in which:

FIG. 1 is a perspective view showing the preferred embodiment of a root canal sterilizing apparatus according to the present invention;

FIG. 2 is an enlarged sectional view of a hand piece for the apparatus shown in FIG. 1;

FIG. 4 is a diagram showing sterilization of the root canal with the present invention;

DETAILED DESCRIPTION OF THE PREFERRED EMBODIMENT

Figure 3:
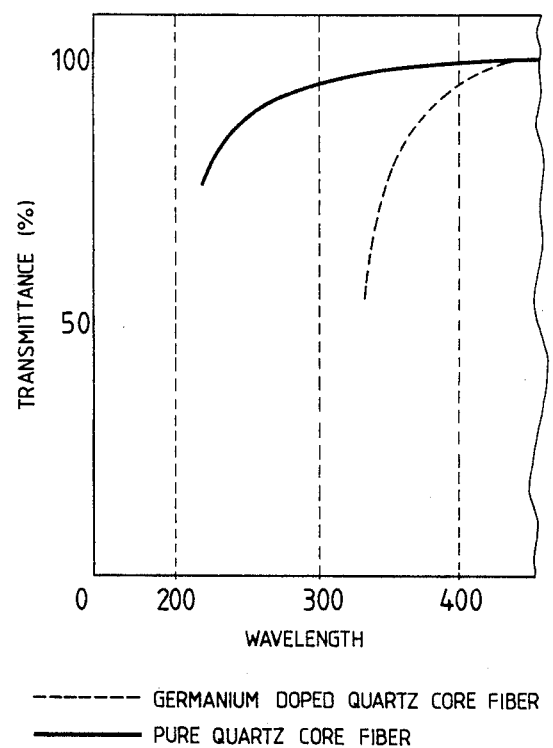
FIG. 3 is a graph showing transmittance as a function of wavelength for a light guide in the apparatus shown in FIG. 1.

FIG. 1 illustrates a root canal sterilizing apparatus according to the preferred embodiment of the invention. Illustrated are a bactericidal ultraviolet ray generating means 1, a light guide 2, a hand piece 3, and a light emitting means 4.

The ultraviolet ray generating means 1 includes an ultraviolet ray generating section made up of a point light source that emits light in a wavelength range of from 200 to 300 nm to light guide 2 with high efficiency using a reflecting condenser mirror and a condenser lens in combination. The point light source may be a high pressure mercury lamp, a mercury xenon lamp, an extra-high pressure mercury lamp, a microwave discharge lamp an excimer laser emitting a light beam of, for instance, 249 nm in wavelength, or other means for producing light of this wavelength. The intensity and wavelength of the emitted light is controlled by a separate control section disposed within ultraviolet ray generating means I. FIG. 1 also illustrates power switch 22, which turns the whole apparatus on or off.

Light guide 2 is an optical fiber that gives needed flexibility. As shown in FIG. 2, light guide 2 is inserted into a flexible metal tube 9 to prevent damage from excessively large external pressure.

In order to minimize less of the bactericidal ultraviolet ray as they pass through light guide 2, a pure quartz core fiber (such as a series of large diameter fibers MS manufactured by Sumitomo Denki Kogyo Co., Ltd.) should be used.

FIG. 3 is a graph showing the transmittance as a function of wavelength per meter of a pure quartz core fiber and a general germanium doped quartz core fiber in which the horizontal axis represents wavelength and the vertical axis transmittance. The pure quartz core fiber's characteristics are indicated by the solid line, and the germanium doped quartz core fiber's characteristics by the broke line. As apparent from FIG. 3, with respect to the light 0.2 to 0.3 μm in wavelength, which is in the range of wavelengths of bactericidal ultraviolet rays, loss is much smaller with the pure quartz core fiber than the germanium doped quartz core fiber.

As shown in FIG. 1, the hand piece 3 is connected to one end of light guide 2, and contains a light emitting means 4 at its opposite end. The operator holds the hand piece 3 to control the areas of the root canal needing sterilization, an operation that will be described in detail later.

FIG. 2 illustrates hand piece 3 and light emitting means 4 in one embodiment in which hand piece 3 acts as a coupling means between light guide 2 and light emitting means 4. Light emitting means 4 is detachably connected to the hand piece body 12 and includes an optical fiber 11 having a pure quartz core that is covered with a stainless steel fiber protecting pipe 18 that serves as a guiding means. Holder 14 slidably holds light emitting means 4 to hand piece body 12. The front end portion of the fiber protecting pipe 18 is bent at about 45°, and optical fiber 11 bends at a similar angle.

The bending angle of θ of fiber protecting pipe 18 should be set to a value for easier insertion into a tooth to be sterilized. This will depend on the position of the tooth. In general, the bending angle is set to 0° for upper jaw anterior teeth and is set to about 45° when used for other teeth. If a plurality of light emitting means 4, different in the bending angle θ, are prepared and selectively used, depending on the teeth to be sterilized, the root canal sterilizing apparatus can be more effectively utilized.

The front end portion of optical fiber 11 protrudes about 20 mm from fiber protecting pipe 18, but is covered with a metal or plastic tube 19 that serves as a covering means, which is flexible to some extent, so that optical fiber 11 is not damaged during use. The outside diameter of tube 19 is 1 mm or less. The configuration of the front end portion of the light emitting means 4 is based on the fact that, in general, the root canal spread has an inside diameter of 1 to 1.5 mm and a depth of less than 20 mm.

Fiber sleeves 16 holds the rear end of the optical fiber 11 and is connected to the rear end of fiber protecting pipe 18 so that the rear end face of fiber sleeve 16 is flush with a rear end face of a fiber sleeve 13 that holds an end optical fiber 11. A compression spring 20 is interposed between fiber sleeve 16 and holder 14 to hold fiber sleeve 16 flush with fiber sleeve 13. Therefore, when light emitting means 4 is engaged with hand piece body 12 as shown in FIG. 2, the rear end face of optical fiber 11 firmly abuts a front end face of the optical fiber of light guide 2.

Light emitting means 4 and hand piece body 12 are joined together with a C-ring 15 on holder 14, which is fitted in a groove formed in the inner wall of hand piece body 12. When holder 14, engaged with hand piece body 12 as shown in FIG. 2, is pulled in the direction of the arrow A, C-ring 15 is flexed, thus disengaging from the groove formed in the inner wall of the hand piece body 12. As a result, light emitting means 4 disengages from the hand piece body 12. Fiber sleeve 16 and fiber protecting pipe 18 secured to the fiber sleeve 16 are pushed inward as one unit by the elastic force of the compression spring 20 during disengagement until a stopper 17, fixedly mounted on fiber protecting pipe 18, strikes against the bottom of a recess formed in the holder 14.

It is also possible to make optical fiber 11 and the optical fiber of light guide 2 from a single optical fiber. The advantage of this construction is that losses will be further reduced. In this case, hand piece 3 does not serve the coupling function of optical fibers in light guide 2 and light emitting means 4. However, the insertion of light emitting means 4 having a separate optical fiber and having different angled fiber protecting pipes 18 that can be attached to hand piece 3 is then more difficult.

FIG. 2 also illustrates that hand piece body 12 is provided with a switch 5 for turning on and off bactericidal ultraviolet ray generating means 1. Switch 5 is connected through an electrical signal wire 8 to the control section of bactericidal ultraviolet ray generating means 1. A timer circuit is built in the control section so that when switch 5 is operated ultraviolet rays are produced for a period of time preset by radiation time setting knob 21, located on bactericidal ultraviolet ray generating means 1 as shown in FIG. 1. The ultraviolet rays thus produced travel through light guide 2, hand piece 3, and emerge from the end of light emitting means 4.

Hand piece body 12 also contains an indication lamp 6, which turns rays. Therefore, after turning on switches, with the end of the light emitting means 4 already set at a desired position in the root canal, the operator can confirm the end of the radiation period because indication lamp 6 will turn off. When the switch 5 is turned off, even during a radiation period radiation is suspended although the timer circuit is in operation.

FIG. 4 is a sectional view showing the end portion of light emitting means 4 inserted into root canal 23, which has been spread. The bactericidal ultraviolet rays emerging from the end of light emitting means 4 are applied deep in root canal 23, thus sterilizing the inside of the root canal.

The following experiment performed by the inventors illustrates the utility of the above described invention.

A 2 m pure quartz core fiber, 0.4 mm in core diameter (the large diameter fiber MS-04 manufactured by Sumitomo Denki Kogyo Co. Ltd.) was used as light guide 2 and optical fiber 11. One end portion, 20 mm in length, of the pure quartz core fiber was inserted into a flexible stainless steel tube having an outside diameter of 0.7 mm and about a 0.1 mm wall thickness, to form lite emitting means 4. The other end of the light emitting means 4 was coupled to a bactericidal ultraviolet ray generating light source, which was a 100 W mercury xenon lamp with a reflecting condenser mirror.

In order to determine whether flexible tube 19 could be smoothly inserted into the root canal, it was inserted into a model of the spread root canal. As a result, it was found that the flexible tube 19 could be inserted smoothly into the model, even if it was a curved root canal because the reinforcing stainless steel tube had a small wall thickness and was flexible.

To detect sterilization efficiency, the intensity of the emergent light was measured. In the measurement, the intensity of light 200 to 300 nm in wavelength was measured. The intensity of bactericidal ultraviolet rays emerging from the end of the light-emergent member was 20 mW/cm$^2$ at 5 mm from the light-emergent end. Bacteria sterilized in root canals are generally concatenate cacci and botryoid cacci, and sterilization of these bacteria require radiation with bactericidal ultraviolet rays of about 10 m$^W$ sec/cm$^2$. Therefore, the obtained intensity was sufficient for sterilization in a short time.

To confirm this, 0.1 m of botryoid cacci, which had 10$^7$/m living bacteria was placed 5 mm from the end of the light guide, and the bactericidal ultraviolet rays was applied. All the botryoid cacci were sterilized in about sixty seconds.

While the invention has been described in connection with what is presently considered to be the most practical and preferred embodiments, it is understood that the invention is not limited to the disclosed embodiment, but, on the contrary, is intended to cover various modifications and equivalent arrangements included within the spirit and scope of the appended claims.

What is claimed is:

1. A method for sterilizing a root canal from bacteria comprising the steps of:
   spreading said root canal;
   guiding a distal end of an optical fiber into said spread root canal; and
   radiating said root canal with bactericidal ultraviolet rays that are generated by a light source, transmitted through said optical fiber, and emitted from an emitting end of said optical fiber to destroy said bacteria.

* * * * *